United States Patent [19]

Stelzer

[11] Patent Number: 5,698,735

[45] Date of Patent: Dec. 16, 1997

[54] PROCESS FOR PREPARING SUBSTITUTED PHENYLACETIC ACID DERIVATIVES AND NOVEL INTERMEDIATES

[75] Inventor: Uwe Stelzer, Leverkusen, Germany

[73] Assignee: Bayer Aktiengesellschaft, Leverkusen, Germany

[21] Appl. No.: 375,871

[22] Filed: Jan. 20, 1995

[30] Foreign Application Priority Data

Jan. 27, 1994 [DE] Germany ............................ 44 02 403.7

[51] Int. Cl.[6] .................................................. C07C 53/134
[52] U.S. Cl. ............................ 562/496; 558/52; 558/388; 560/103; 564/182
[58] Field of Search ...................... 558/388; 560/19; 562/496; 564/182

[56] References Cited

U.S. PATENT DOCUMENTS 4,707,549  11/1987  Fritz et al. ............................ 544/336

FOREIGN PATENT DOCUMENTS

| 633761 | 12/1963 | Belgium . |
| 220947 | 5/1987 | European Pat. Off. . |
| 310186 | 5/1989 | European Pat. Off. . |
| 377893 | 7/1990 | European Pat. Off. . |
| 410590 | 1/1991 | European Pat. Off. . |
| 1374655 | 11/1963 | France . |
| 53-12837 | 2/1978 | Japan . |
| 62-126159 | 6/1987 | Japan . |
| 971700 | 9/1964 | United Kingdom . |

OTHER PUBLICATIONS

Morrison, Boyd, Organic Chemistry; p. 164 Year Not Available.

Tetrahedron Letters, vol. 32, No. 41, pp. 5741–5744, Month Not Available 1991 (Silveira).

A. Fokin, et al.,Izu. Akad. Nauk SSR, Ser. Khim., No. 4, pp. 806–809, Month Not Available (1979).

Chemical Abstracts, vol. 90—Abstract No. 168,303h, Abstract of JP 78–149,945 Month Not Available (1979).

Chemical Abstracts, vol. 89, Abstract No. 23975y, Abstract of JP 78–12,837 Month Not Available (1978).

J. Lichtenberger et al., Bull. Chem. Soc. Fr., No. 9–10, pp. 995–1001 Month Not Available (1948).

Chemical Abstracts. vol. 91, Jul. 16, 1979, No. 3, Abstract No. 19832y, abstract of Izu. Akad. Nauk SSSR. Ser. Khim, 1979(4), pp. 806–809.

Chemical Abstracts, vol. 107, Abstract No. 197813z, Abstract of JP 62–126,159 Month Not Available (1987).

*Primary Examiner*—Johann Richter
*Assistant Examiner*—Laura L. Stockton
*Attorney, Agent, or Firm*—Sprung Kramer Schaefer & Briscoe

[57] ABSTRACT

Description here is a novel process for preparing phenyl acetic acid derivatives of the formula (I)

$$Ar-CH_2-R^1 \qquad (I)$$

in which Ar and $R^1$ are as defined in the description by reaction of sulfonyloxy-activated hydroxyacetic acid derivatives of the formula (II)

$$R^3-SO_2-O-CH_2-R^1 \qquad (II)$$

in which $R^3$ is as defined in the description. with aromatics of the formula (III)

$$Ar-H \qquad (III)$$

has been found. The intermediates of the formula (II), some of which are novel, are obtained from hydroxyacetic acid derivatives by reaction with sulfonyl halides or sulfonic anhydrides. The phenylacetic acid derivatives are important starting materials for preparing pesticides.

2 Claims, No Drawings

PROCESS FOR PREPARING SUBSTITUTED PHENYLACETIC ACID DERIVATIVES AND NOVEL INTERMEDIATES

The invention relates to a novel process for preparing phenylaceic acid derivatives which are unsubstituted in the α position and known in part, to novel intermediates and to a process for their preparation.

It is known that substituted phenylacetic acids and derivatives thereof are obtained by chloromethylating or bromomethylating suitably substituted aromatics to give chloromethylated or bromomethylated aromatics which are then reacted with cyanides, followed by hydrolysis to give the acid (see, for example, J. Org. Chem. 58, 1262 (1993), Houben-Weyl, Methoden der Organischen Chemie, [Methods of Organic Chemistry], Georg Thieme Verlag, Stuttgart, Volume 5/4 page 484, 1960, Houben-Weyl, Methoden der Organischen Chemie, [Methods of Organic Chemistry], Georg Thieme Verlag, Stuttgart, Volume VIII, page 427, 1952). However, this method has the disadvantage that owing to the potential formation of the cancerogenic bis(halogenomethyl) ethers during halogenomethylation, more extensive safety precautions must be taken when carrying out the reaction.

The publication J. Org. Chem. 1991, 56, 183–187 describes the preparation of 2-arylpropionic esters and 2-aryl-butyric esters by alkylation of aromatic compounds with the corresponding 2-(sulfonyloxy)propionic esters or 2-(sulfonyloxy)butyric esters in the presence of $AlCl_3$. The synthesis of phenylacetic acids which are unsubstituted in the α position is not described (see also, for example, Org. Prep. Proc. Int. 1989, 21 (3), 375–376, J. Amer. Chem. Soc. 113, 9630 (1991), Tetrahedron Lett., 26, 477 (1985), J. Med. Chem. 24, 382 (1981), J. Amer. Chem. Soc. 95, 3340 (1973)).

Furthermore, it is known that phenylacetic acids are obtained by carboxylation of benzyl halides under phase transfer conditions (Tetrahedron Lett., 24 (37), 4005–4008 (1983); J. Chem. Soc., Chem. Commun., (24), 1090–1091 (1978)). A substantial disadvantage of these methods is, apart from using iron carbonyls and cobalt carbonyls, the fact that they must be in part carried out under pressure and that they lead to reaction mixtures.

The present invention provides (1) a process for preparing phenylacetic acid derivatives of the formula (I)

$$Ar-CH_2-R^1 \quad (I)$$

in which

Ar represents phenyl which is unsubstituted or is substituted by one to five identical or different substituents, possible substituents being: halogen, alkyl, alkoxy, halogenoalkyl, halogenoalkoxy, alkylcarbonylamino, dialkylamino, substituted or unsubstituted aryl and substituted or unsubstituted aryloxy and $R^1$ represents cyano, aminocarbonyl, alkylaminocarbonyl, dialkylaminocarbonyl or a group $-COOR^2$, in which $R^2$ represents hydrogen, substituted or unsubstituted alkyl, alkenyl, halogenoalkyl or represents in each case substituted or unsubstituted aryl or aralkyl, which comprises reacting sulfonyloxy-activated hydroxyacetic acid derivatives of the formula (II)

$$R^3-SO_2-O-CH_2-R^1 \quad (II)$$

in which $R^1$ is as defined above and $R^3$ represents halogen, alkyl, halogenoalkyl, or represents in each case substituted or unsubstituted aryl or benzyl with aromatics of the formula (III)

$$Ar-H \quad (III)$$

in which

Ar is as defined above, if desired in the presence of a diluent and in the presence of an acid, and then, if desired, hydrolyzing the resulting product;

(2) a process for preparing sulfonylated n-butyl glycolates of the formula (IIa)

$$R^3-SO_2-O-CH_2-\underset{\underset{O}{\|}}{C}-OC_4H_9n \quad (IIa)$$

in which $R^3$ is as defined above, which comprises reacting n-butyl glycolates of the formula (IV)

$$HO-CH_2-\underset{\underset{O}{\|}}{C}OC_4H_9n \quad (IV)$$

with sulfonyl halides of the formula (Va)

$$R^5-SO_2-Hal \quad (Va) \; or$$

with sulfonic anhydrides of the formula (Vb)

$$(R^3-SO_2)_2O \quad (Vb)$$

in which $R^3$ is as defined above and

Hal represents fluorine, chlorine or bromine, in particular fluorine or chlorine, if desired in the presence of a diluent and, if desired, in the presence of acid-binding agents;

(3) novel phenylacetic esters of the formula (Ia)

$$Ar^1-CH_2-COOC_4H_9n \quad (Ia)$$

in which $Ar^1$ represents phenyl which is substituted by three identical or different $C_1-C_6$-alkyls;

(4) novel sulfonylated n-butyl glycolates of the formula (IIa)

$$R^3-SO_2-O-CH_2-\underset{\underset{O}{\|}}{C}-OC_4H_9n \quad (IIa)$$

in which $R^3$ is as defined above, with the exception of the compound n-butyl [(fluorosulfonyl) oxy]acetate (Izv. Akad. Nauk. SSSR, Ser. Khim., (4), 806–809, 1979).

It must be regarded as extremely surprising that the process according to the invention (1) provides the phenylacetic acid derivatives of the formula (I) in very good yields and in high purity through a Friedel-Crafts alkylation with sulfonyloxyacetic acid derivatives since under these reaction conditions a higher proportion of undesirable by-products and in conjunction therewith poorer yields must usually be expected. A further advantage of the process according to the invention is that the formation of the strongly cancerogenic bis(halogenomethyl) ether, which is formed when phenylacetic acid derivatives are prepared via chloromethylation of aromatics as the intermediate step, is avoided. Accordingly, the novel process can be carried out under significantly improved safety and environmental aspects.

Compared with the prior art methods, the process according to the invention also turns out to be a significantly lower-cost synthetic route to phenylacetic acid derivatives of the formula (I) and thus represents a valuable addition to the prior art.

The compounds prepared by the process according to the invention are preferably compounds of the formula (I) in which Ar represents phenyl which is unsubstituted or substituted by one to three identical or different substituents, possible substituents being: fluorine, chlorine, bromine, $C_{1-4}$-alkyl, $C_{1-4}$-alkoxy, $C_{1-4}$-halogenoalkyl, $C_{1-4}$-halogenoalkoxy, $C_{1-4}$-alkylcarbonylamino, di-$C_1$–$C_4$-alkylamino, or represents in each case unsubstituted or halogen- or $C_1$–$C_6$-alkyl-substituted phenyl and phenyloxy and $R^1$ represents cyano, aminocarbonyl, methylaminocarbonyl, dimethylaminocarbonyl, or a group —$COO^2$, in which $R^2$ represents hydrogen, $C_{1-18}$-alkyl, $C_3$-$C_6$-alkenyl, fluorine- or chlorine-substituted $C_{1-18}$-alkyl or represents in each case unsubstituted or halogen- or $C_1$–$C_6$-alkyl-substituted phenyl or benzyl.

The compounds prepared by the process according to the invention are particularly preferably compounds of the formula (I) in which Ar represents phenyl which is unsubstituted or substituted by one to three identical or different substituents, possible substituents being: fluorine, chlorine, bromine, methyl, ethyl, n- and i-propyl, n-, i-, s- and tert.-butyl, methoxy, ethoxy, trifluoromethyl, difluoromethyl, trifluoromethoxy, difluoromethoxy, methylcarbonylamino, or represents in each case unsubstituted or fluorine-, chlorine-, bromine-, CN—, $NO_2$—, methyl-, methoxy-, methylthio-, trifluoromethyl-, trifluoromethoxy-substituted phenyl and phenyloxy and $R^1$ represents cyano or aminocarbonyl, carboxyl, methoxycarbonyl, ethoxycarbonyl, n- or i-propyloxycarbonyl, n-, i-, s- or tert.-butyloxycarbonyl, pentyloxy- or hexyloxycarbonyl.

Very particularly preferably, the process according to the invention relates to the preparation of compounds of the formula (I) in which Ar represents 2,4,6-trimethylphenyl and $R^1$ represents cyano or carboxyl, methoxycarbonyl, ethoxycarbonyl or n-butyloxycarbonyl.

The definitions of radicals listed above in general or mentioned as being preferred apply not only to the end products of the formula (I) but also analogously to the starting materials or intermediates required for the synthesis in each case.

These definitions of radicals can be combined as desired among themselves but also among the particular ranges and preferred ranges.

If, for example, mesitylene and n-butyl methylsulfonyloxyacetate are used as starting materials and aluminum chloride as Lewis acid, the reaction sequence of the process according to the invention can be represented by the following scheme:

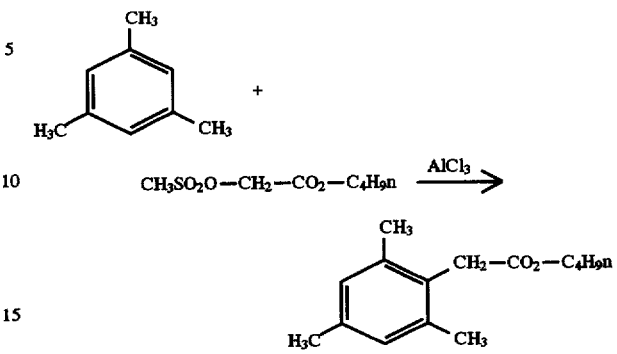

A general definition of the sulfonyloxy-activated hydroxyacetic acid derivatives to be used as starting materials in the process according to the invention listed above under (1) for preparing the compounds of the formula (I) is provided by the formula (II). In the formula (II), $R^1$ and $R^3$ preferably or in particular have the meaning already mentioned above as preferred or in particular as preferred for $R^1$ and $R^3$ in conjunction with the description of the compounds of the formula (I) and (II).

Some of the sulfonyloxy-activated hydroxyacetic acid derivatives of the formula (II) are already known in principle from the literature (see, for example, DE 2431734, JP 59010564, JP 59010564, U.S. Pat. No. 4,260,555, Bull. Chem. Soc. Jpn. 43, 1572–1573, (1970), J. Phys. Chem. 94, 8835–8839, (1990), J. Org. Chem. 42, 3109–3113, (1977), Izv. Akad. Nauk SSSR, Ser. Khim (7), 1682, 1983). The sulfonyloxy-alkylated hydroxyacetic acid derivatives of the formula (II) which are known and those which are not yet known can be obtained by the process according to the invention described under (2).

A general definition of the aromatics to be used as starting materials in the process shown above under (1) is provided by the formula (III). In the formula (III), Ar preferably or particularly preferably has the meaning already mentioned above as preferred or particularly preferred for Ar in conjunction with the description of the compounds of the formula (I).

The aromatics of the formula (III) are known synthetic chemicals.

The process according to the invention described under (1) is preferably carried out in the presence of a diluent. Suitable diluents for carrying out the process described under (1) are any common organic solvents which are inert under the reaction conditions. They include, for example, in particular inert solvents, such as hydrocarbons, halogenated hydrocarbons, nitroalkanes and nitroaromatics. Examples are hexane, cyclohexane, dichloroethane, chloroform, carbon tetrachloride, nitromethane or nitrobenzene. It is particularly advantageous to use the aromatics of the formula (III) required for the reaction in accordance with the process according to the invention described under (1) themselves as diluents.

When carrying out the process according to the invention described under (1), the reaction temperatures can be varied over a fairly wide range. In general, the reaction is carried out at temperatures between –20° C. and 200° C., preferably at temperatures between 0° C. and 150° C.

The process according to the invention described under (1) is in general carried out at atmospheric pressure. However, alternatively it can also be carried out under superatmospheric or reduced pressure.

The process step according to the invention described under (1) is carried out in the presence of strong acids. Examples of such acids include: Lewis acids, such as, for example, aluminum chloride, aluminum bromide, antimony trichloride, ferric chloride, tin tetrachloride, zinc chloride, titanium tetrachloride, boron trichloride or boron trifluoride; mineral acids, such as, for example, sulfuric acid or hydrochloric acid, which, if desired, may also be used in gaseous form, and sulfonic acids, such as, for example, p-toluenesulfonic acid or trifluoromethanesulfonic acid. Preferably, Lewis acids are used, aluminum chloride being particularly preferred.

1.0–10.0 mol, preferably 2.3 to 4.0 mol, particularly preferably 2.75 to 4.0 mol of Lewis acid, mineral acid or sulfonic acid and 1 to 20 mol of the aromatic are used, for example, per mole of sulfonyloxy-activated hydroxyacetic acid derivatives of the formula (II) in 50–500 ml of one of the abovementioned diluents.

In a preferred embodiment, the process according to the invention described under (1) is carried out in such a manner that the corresponding aromatic of the formula (III) is first introduced itself as diluent or dissolved in one of the abovementioned solvents together with a Lewis acid, such as, for example, aluminum chloride, the sulfonyloxy-activated hydroxyacetic acid derivative of the formula (II) is then added, and then the resulting mixture is stirred at the stated temperature until the reaction is complete.

Depending on the starting materials and the reaction conditions selected, either phenylacetic esters, the phenylacetic acid or phenylacetonitrile can be obtained.

In a further embodiment, the process according to the invention described under (1) is carried out by first introducing the sulfonyloxy-activated hydroxyacetic acid derivatives of the formula (II) and the aromatics of the formula (III), if desired, dissolved in a solvent, then adding a Lewis acid or a mineral acid or a sulfonic acid, and stirring the resulting mixture at the stated temperature until the end of the reaction.

Workup can take place by customary methods, for example by hydrolysis with 10% hydrochloric acid, extraction with an organic, virtually water immiscible solvent, drying of the organic phase and removal of the solvent under reduced pressure. The crude product thus obtained can be purified by recrystallization, chromatography or distillation.

In a further embodiment, the crude product (ester or nitrile) obtained by the process (1) described above can, if desired, be hydrolyzed by acid or alkaline hydrolysis to give substituted phenylacetic acids or phenyl aceramides. Hydrolysis takes place by generally known methods (see, for example, Houben-Weyl, Methoden der Organischen Chemie, [Methods of Organic Chemistry], Georg Thieme Verlag, Stuttgart, Volume VIII, page 427, and Bl. Soc. Chim. Belg., 64, page 91, (1954), J. Am. Chem. Soc. 72, 4091 (1950), Org. Synth. Coll. Vol. III 557, 558 (1955)). by, for example, adding 1 mol of the crude product obtained by the process (1) described above to a solution of 1–50 mol of sodium hydroxide in methanol/water and stirring the resulting mixture at temperatures between 20° C. and 150° C. for several hours. For workup, the reaction mixture is extracted with a virtually water-immiscible solvent, the aqueous phase is acidified with mineral acid, and the product is filtered off or extracted.

However, it may also be advantageous to react the crude product (ester or nitrile) obtained by the process (1) described above with mineral acids, such as, for example, concentrated sulfuric acid or hydrochloric acid, in water at temperatures between 20° C. and 150° C. The product is isolated by filtration or extraction.

The purity of the end products obtained by the acid or alkaline hydrolysis described above of the crude products of the formula (I) can, if desired, be increased further by customary methods, such as, for example, distillation, chromatography or crystallization.

The n-butyl glycolate of the formula (IV) to be used as starting material in the process mentioned above under (2) is a generally known compound of organic chemistry.

A general definition of the sulfonyl halides and sulfonic anhydrides also required as starting materials in the process mentioned above under (2) is provided by the formulae (Va) and (Vb). In the formulae (Va) and (Vb), $R^3$ preferably or in particular has the meaning already mentioned above as preferred or particularly preferred for $R^3$ in conjunction with the description of the compounds of the formula (II). Hal represents fluorine, chlorine or bromine, preferably fluorine or chlorine.

The sulfonyl halides of the formula (Va) and the sulfonic anhydrides of the formula (Vb) are known synthetic chemicals.

The process according to the invention described under (2) for preparing sulfonylated n-butyl glycolates of the formula (IIa) is preferably carried out in the presence of a diluent. Suitable diluents are any customary organic solvents which are inert under the reaction conditions. Useful solvents are preferably aromatic or aliphatic hydrocarbons such as toluene, benzene, n-hexane, cyclohexane, halogenated hydrocarbons, such as methylene chloride, chloroform, carbon tetrachloride, chlorobenzene and o-dichlorobenzene, furthermore ketones, such as acetone and methyl isopropyl ketone, furthermore ethers, such as diethyl ether, tetrahydrofuran and dioxane, moreover carboxylic esters, such as ethyl acetate, and also strongly polar solvents, such as dimethyl sulfoxide and sulfolane. If the hydrolysis stability of the acid halide permits, the reaction can also be carried out in the presence of water.

The process according to the invention described under (2) is preferably carried out in the presence of acid-binding agents. They include, in particular, alkali metal carbonates, such as potassium carbonate, alkaline earth metal carbonates, such as calcium carbonate, alkali metal hydroxides, such as sodium hydroxide and potassium hydroxide, alkaline earth metal oxides, such as magnesium oxide and calcium oxide, aliphatic, aromatic or heterocyclic amines, such as trimethylamine, triethylamine, N,N-dimethylaniline, N,N-dimethylbenzylamine, diazobicyclooctane (DABCO), diazabicycloundecene (DBU), pyridine, 2-methyl-5-ethyl-pyridine, lutidine, 2,4,6-trimethylpyridine, 4-dimethylamino-pyridine and imidazoles.

When carrying out the process according to the invention described under (2), the reaction temperatures can be varied over a fairly wide range. In general, the reaction is carried out at temperatures between −50° C. and +50° C., preferably at temperatures between −20° C. and room temperature.

The process according to the invention described under (2) is in general carried out at atmospheric pressure. However, alternatively, it can also be carried out under superatmospheric or reduced pressure.

When carrying out the process according to the invention described under (2), for example, 1 mol of n-butyl hydroxyacetate of the formula (IV) are reacted with 1 to 5 mol, preferably 1 to 2 mol, of sulfonyl halide of the formula (Va) or with 1 to 5 mol, preferably 1 to 2 mol of sulfonyl halide of the formula (5a) or with 1 to 5 mol, preferably 1 to 2 mol, of sulfonic anhydride of the formula (Vb) and with 1 to 5 mol, preferably 1 to 2 mol, of an acid-binding agent in 100 to 500 ml of the diluent.

In a preferred embodiment of the process according to the invention described under (2), the n-butyl glycolate of the formula (IV) is introduced first together with the acid-binding agent in one of the abovementioned inert organic solvents and in the temperature range given, and with the sulfonyl halide of the formula (Va) or the sulfonic anhydride of the formula (Vb) is added. Stirring of the reaction mixture is continued for a few hours. Workup can take place by customary methods, for example by hydrolysis of the reaction mixture, extraction of the aqueous phase with a virtually water-immiscible organic solvent, such as, for example, diethyl ether or methylene chloride and drying of the organic phases. The solvent is removed by subsequent distillation under reduced pressure. The crude product thus obtained can be directly used further as starting material in accordance with the process according to the invention described under (1) or be further purified by distillation, crystallization or chromatography.

A general definition of the phenylacetic acid derivatives mentioned under (3) is provided by the formula (Ia)

$Ar^1$ preferably represents phenyl which is substituted by three identical or different $C_1$–$C_8$-alkyls.

$Ar^1$ particularly preferably represents phenyl which is substituted by three identical or different $C_1$–$C_6$-alkyls.

$Ar^1$ particularly preferably represents phenyl which is substituted by three identical or different substituents selected from methyl, ethyl, n- or i-propyl.

The phenylacetic acid derivatives of the formula (Ia) are novel and are provided by the invention. They can be obtained by the process according to the invention (1).

A general definition of the sulfonylated n-butyl glycolates mentioned under (4) is provided by the formula (IIa).

$R^3$ preferably represents chlorine, bromine, $C_1$–$C_8$-alkyl, $C_1$–$C_8$-halogenoalkyl or represents in each case phenyl or benzyl each of which is unsubstituted or substituted by one to three identical or different substituents selected from cyano, nitro, halogen, $C_1$–$C_8$-alkyl, $C_1$–$C_8$-alkoxy or $C_1$–$C_8$-halogenoalkoxy.

$R^3$ particularly preferably represents chlorine, bromine, methyl, ethyl, n- or i-propyl, n-, s-, i- or t-butyl each of which is unsubstituted or substituted by one or more substituents selected from fluorine, chlorine and/or bromine, or represents phenyl which is unsubstituted or substituted by one to three identical or different substituents selected from cyano, nitro, chlorine or bromine or substituted by methyl, ethyl, n- or i-propyl, n-, s-, i- or t-butyl each of which is unsubstituted or substituted by one or more substituents selected from fluorine, chlorine and/or bromine.

The sulfonylated n-butyl glycolates of the formula (IIa) have not yet been disclosed in the literature, with the exception of the compound n-butyl [(fluorosulfonyl)oxy]-acetate (Izv. Akad. Nauk. SSSR, Ser. Khim., (4), 806–809, 1979). They are provided by the present invention as novel substances and can be prepared in accordance with the process described above under (2).

The substituted phenylacetic acid derivatives of the formula (I) to be prepared by the process according to the invention can be used as starting materials for preparing herbicides and pesticides (see, for example, EP-A 528156).

PREPARATION EXAMPLES

Example II-1

CH₃SO₂OCH₂COOCH₃

18 g (0.2 mol) of methyl hydroxy acetate are first introduced into 250 ml of dichloromethane, and the resulting solution is cooled to 0° C. 20.2 g (0.2 mol) of triethylamine are added to this solution, and 34.3 g (0.3 mol) of methanesulfonyl chloride are added dropwise at 0° C. over a period of one hour. The batch is stirred at 0° C. overnight, ice water is added, the aqueous phase is extracted several times with dichloromethane, and the combined organic phases are dried over sodium sulfate. After filtering of the drying agent and distilling off the solvent, a fine-vacuum distillation is carried out. 29.7 g (88% of theory) of methyl methylsulfonyloxy acetate having a GC content of >98% are isolated at a boiling point of 98°–101° C./0.1 mbar as a colorless oil.

Example II-2

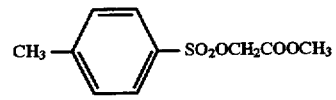

18 g (0.2 mol) of methyl hydroxyacetate and 20.2 g (0.2 mol) of triethylamine are first introduced into 300 ml of dichloromethane at 0° C. 41.9 g (0.22 mol) of toluenesulfonyl chloride are then added at this temperature in small portions. Stirring of the batch at 0° C. is continued overnight. Ice water is added, the phases are separated, and the aqueous phase is extracted three times with dichloromethane. The combined organic phases are washed once with water, dried, and the solvent is removed on a rotary evaporator. 48 g (98% of theory) of methyl toluenesulfonyloxyacetate having a GC content of 96% are isolated as a colorless solid.

Example II-a-1

CH₃SO₂OCH₂COO-nC₄H₉

27.8 g (0.2 mol) of n-butyl hydroxyacetate (95% pure by GC) and 20.2 g (0.2 mol) of triethylamine are first introduced into 300 ml of dichloromethane at −5° C. 34.4 g (0.3 mol) of methanesulfonyl chloride in 50 ml of dichloromethane are slowly added dropwise at 0° to 5° C. Stirring of the batch at 0° C. is continued overnight, ice water is added, the phases are separated, and the aqueous phase is extracted twice with dichloromethane. The combined organic phases are dried, and the solvent is removed on a rotary evaporator leaving a colorless oil which is subjected to incipient distillation in vacuo. n-Butyl methylsulfonyloxyacetate is isolated as an almost colorless oil (40.5 g, 96.3% of theory, GC content 91%).

¹H NMR* (δ=0.946 (t, 3H, CH₃), 1.33–1.45 (m, 2H, CH₂), 1.61–1.706 (m, 2H, CH₂), 3.21 (s, 3H, CH₃), 4.22 (t, 2H, CH₂), 4.77 (s, 2H, CH₂)).

Example II-a-2

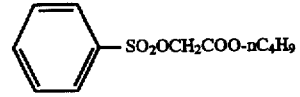

45.8 g (84% of theory) of n-butyl phenylsulfonyloxyacetate are obtained from 27.8 g (0.2 mol) of n-butyl hydroxyacetate, 46 g (0.26 mol) benzylsulfonyl chloride and 20.2 g (0.2 mol) of triethylamine using the same method.

¹H NMR* (δ=0.83 (t, 3H, CH₃), 1.19–1.31 (m, 2H, CH₂), 1.45–1.55 (m, 2H, CH₂), 4.05 (t, 2H, CH₂), 4.54 (s, 2H, CH₂), 7.47–7.89 (m, 5H, phenyl)).

Example I-1

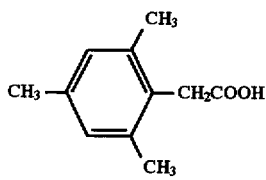

39.9 g (0.3 mol) of aluminum chloride are first introduced into 200 ml of mesitylene, and the mixture is heated to 40°–45° C. It is stirred for 0.5 hour, and 22.0 g (0.1 mol) of n-butyl methylsulfonyloxyacetate (GC content 91%, 0.095 mol) are added dropwise at the stated temperature over a period of 1 hour. The batch is additionally stirred at 40°–45° C. overnight and then hydrolyzed with 10% hydrochloric acid. The organic phase is separated off, the aqueous phase is extracted twice with diethyl ether, the organic phases are combined and dried. After distilling off the solvent and the mesitylene, 12 g of NaOH in 25 ml of water and 80 ml of methanol are added to the oily crude product obtained, and the mixture is refluxed for 5 hours. The reaction solution is poured into water, extracted twice with diethyl ether, and the aqueous phase is acidified with concentrated hydrochloric acid. The aqueous phase is extracted several times with methylene chloride, the organic phases are combined and dried, and after distilling off the solvent 14.0 g of mesitylacetic acid 82.7% of theory, GC content 96%) are isolated.

Example I-2

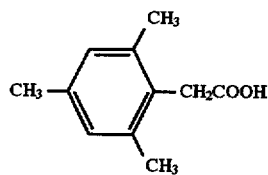

79.8 g (0.6 mol) of aluminum chloride are first introduced into 400 ml of mesitylene, and the resulting mixture is heated to 40°–45° C. It is additionally stirred for one hour, and 33.6 g (0.2 mol) of methyl methylsulfonyloxy acetate (98% pure by GC) are added dropwise at the stated temperature over a period of 2 to 3 hours. The batch is additionally stirred at 40°–45° C. overnight and then hydrolyzed with 10% hydrochloric acid. The organic phase is separated off, and the aqueous phase is extracted twice with diethyl ether or dichloromethane, the organic phases are combined and dried. After distilling off the more volatile solvent, 38.7 g of an oily crude product are obtained. To isolate the ester, this crude product can be distilled or converted into mesitylacetic acid by refluxing it (5 hours) together with 25 g of NaOH in 50 ml of water and 160 ml of methanol. The reaction solution is poured into water, the resulting mixture is extracted twice with diethyl ether, and the aqueous phase is then acidified with concentrated hydrochloric acid. The precipitated product is filtered off with suction. It is extracted several times with dichloromethane, the organic phases are combined and dried, and after distilling off the solvent 30 g of mesitylacetic acid (84.2% of theory, GC content 96%) are isolated.

Example I-3

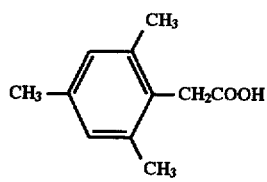

7.8 g (0.133 mol) of aluminum chloride are first introduced into 100 ml of mesitylene, and the resulting mixture is heated to 40°–45° C. 10 g (0.044 mol) of methyl p-toluenesulfonyloxyacetate are added dropwise over a period of 1 to 2 hours. The mixture is additionally stirred at 40°–45° C. overnight, hydrolyzed with 100 ml of 10% hydrochloric acid, the organic phase is separated off, the aqueous phase is extracted twice with methylene chloride, and the organic phases are combined and dried. After distilling off the solvent, the oily crude product is refluxed and stirred directly with 6 g of NaOH in 20 ml of water and 50 ml of methanol for 3 hours. The reaction solution is poured into water, the mixture is extracted twice with diethyl ether, and the aqueous phase is then acidified with concentrated hydrochloric acid. The mixture is extracted three times with dichloromethane, the organic phases are combined and dried, and after distilling off the solvent 6.6 g (83% of theory) of mesitylacetic acid are isolated.

Example I-4

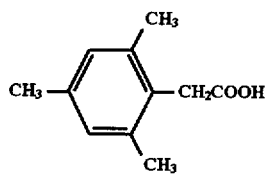

8.0 g (0.06 tool) and 5.4 g (0.0198 mol) of n-butyl phenylsulfonyloxyacetate are reacted in 60 ml of mesitylene by the method of Example 7, and the reaction mixture is hydrolyzed with 5 g of NaOH in 15 ml of water and 50 ml of methanol to give the acid. 3.0 g (85% of theory) of mesitylacetic acid are isolated.

Example Ia-1

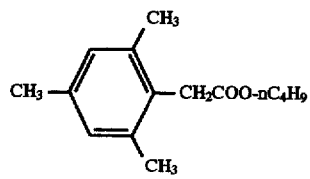

20 g (0.15 mol) of aluminum chloride are first introduced into 100 ml of mesitylene, and the resulting mixture is heated to 40°–45° C. 10.6 g (0.05 mol) of n-butyl methylsulfonyloxy acetate are added dropwise over a period of one hour. The mixture is additionally stirred overnight, then hydrolyzed with 100 ml of 10% hydrochloric acid, the organic phase is separated off, and the aqueous phase is extracted with methylene chloride. The organic phase is dried, and the solvent is separated off. Petroleum ether is added several times to the crude product obtained and the remaining colorless solid is separated off. In this manner, 1.3 g (14% of theory) of mesitylacetic acid are isolated directly. The petroleum ether phase is concentrated, and the crude produce is distilled in vacuo (0.01 mbar, b.p. 120° C.). 8.8 g (75.1% of theory) of n-butyl mesityl acetate are isolated.

$^1$H NMR* ($\delta$=0.90 (t, 3H, CH$_3$), 1.29–1.37 (m, 2H, CH$_2$), 1.54–1.61 (m, 2H, CH$_2$), 2.25 (s, 3H, CH$_3$), 2.29 (s, 6H, 2×CH$_3$), 3.63 (s, 2H, CH$_2$), 4.07 (t, 2H, CH$_2$), 6.85 (m, 2H, aromat protons)).

Example I-5

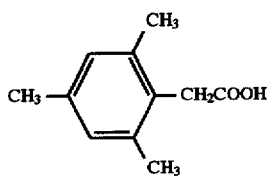

8.0 g (0.06 mol) of aluminum chloride are first introduced into 40 ml of mesitylene, the resulting mixture is heated to 40°–45° C. 4.1 g (0.02 mol) of phenylsulfonyloxyacetonitrile are added, and the mixture is stirred at 40°–45° C. for 6 hours. 100 ml of 10% hydrochloric acid are then added, and the reaction mixture is extracted several times with methylene chloride. The organic phases are dried, the crude product obtained after distilling off the solvent is refluxed together with 9 ml of concentrated sulfuric acid in 11 ml of water for 6 hours, ice water is added, the mixture is made alkaline with NaOH and extracted with diethyl ether. The aqueous phase is acidified with concentrated hydrochloric acid and extracted three times with methylene chloride, and the organic phase is dried. After distilling off the solvent, 2.3 g (62% of theory) of mesitylacetic acid are isolated.

Example I-6

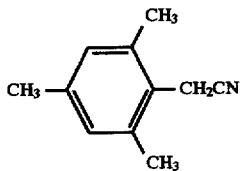

8.0 g (0.06 mol) of aluminum chloride are first introduced into 40 ml of mesitylene at 0° C. 4.1 g (0.02 mol) of phenylsulfonyloxyacetonitrile are then added, and the reaction mixture is stirred at room temperature overnight. The crude product obtained after hydrolysis is chromatographed on silica gel using dichloromethane. 2.3 g (72.3% of theory) of 2,4,6-trimethylbenzyl cyanide are isolated.

Example I-7

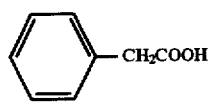

19.15 g (0.144 mol) of aluminum chloride are first introduced into 70 ml of benzene at 40°–50° C., and 10 g (0.048 mol) of n-butyl methanesulfonyloxyacetate are then added. The mixture is additionally stirred overnight, hydrolyzed with 10% hydrochloric acid and worked up by the method of Examples 6 to 9. The crude product obtained is refluxed together with 6 g of NaOH in 15 ml of water and 50 ml of methanol for 5 hours. Further workup is carried out as in Examples 6 to 9. 5.17 g (90.3% of theory) of phenylacetic acid are isolated.

*) $^1$H NMR spectra were recorded in deuterochloroform (CDCl$_3$) with tetramethylsilane (TMS) as the internal standard. The chemical shift is given as $\delta$ value in ppm.

What is claimed is:

1. A process for preparing phenylacetic acid derivative of the formula

Ar—CH$_2$—COOH in which

Ar represents 2,4,6-trimethylphenyl which comprises reacting sulfonyloxy-activated hydroxyacetic acid derivatives of the formula

R$^3$—SO$_2$—O—CH$_2$—R$^1$     (II)

in which

R$^1$ represents cyano, methoxycarbonyl, ethoxycarbonyl or n-butyloxycarbonyl and R$^3$ represents halogen, alkyl, halogenoalkyl, or represents in each case substituted or unsubstituted aryl or benzyl with the aromatic of the formula Ar—H     (III)

in which

Ar is as defined above, optionally in the presence of a diluent and in the presence of 2.3 to 4.0 mole aluminum chloride per mole of the compound of formula (II), and then hydrolyzing the resulting product.

2. The process according to claim 1, wherein the temperature of the reaction is between −50° C. to +50° C. and 2.75 to 4.0 mole of AlCl$_3$ per mol of the compound of formula II is employed.

* * * * *